(12) United States Patent
Schomaker et al.

(10) Patent No.: US 10,676,449 B2
(45) Date of Patent: *Jun. 9, 2020

(54) ELECTRONICALLY ACTIVATED STRAINED ALKYNES

(71) Applicant: Wisconsin Alumni Research Foundation, Madison, WI (US)

(72) Inventors: Jennifer M. Schomaker, Madison, WI (US); Eileen G. Burke, Somerville, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/284,258

(22) Filed: Feb. 25, 2019

(65) Prior Publication Data

US 2019/0233385 A1 Aug. 1, 2019

Related U.S. Application Data

(63) Continuation-in-part of application No. 15/873,984, filed on Jan. 18, 2018, now Pat. No. 10,233,162.

(60) Provisional application No. 62/447,466, filed on Jan. 18, 2017.

(51) Int. Cl.
*C07D 291/02* (2006.01)

(52) U.S. Cl.
CPC .................. *C07D 291/02* (2013.01)

(58) Field of Classification Search
CPC .................................................. C07D 291/02
See application file for complete search history.

(56) References Cited

PUBLICATIONS

Burke. Journal of the American Chemical Society, 2017, 139, 8029-37 (Year: 2017).*
Baskin, J. M.; Bertozzi, C. R. (2007) "Bioorthogonal Click Chemistry: Covalent Labeling in Living Systems," *QSAR Comb. Sci.* 26:1211-1219.
Castro, Rodríguez and Albericio (2016) "CuAAC: An Efficient Click Chemistry Reaction on Solid Phase," *ACS Comb. Sci.* 18(1):1-14.
Codelli, J. A.; Baskin, J. M.; Agard, N. J.; Bertozzi, C. R. (2008) "Second-Generation Difluorinated Cyclooctynes for Copper-Free Click Chemistry," *J. Am. Chem. Soc.* 130:11486-11493.
Evans, R. A. (2007) "The Rise of Azide-Alkyne 1,3-Dipolar 'Click' Cycloaddition and its Application to Polymer Science and Surface Modification," *Australian Journal of Chemistry* 60(6): 384-395.
Greene's Protective Groups in Organic Synthesis, ISBN-13: 978-1118057483, © 2014, John Wiley & Sons, Inc. (In particular, see Chapter 1, Protecting Groups: An Overview, Chapter 2, Hydroxyl Protecting Groups,Chapter 4, Carboxyl Protecting Groups, and Chapter 5, Carbonyl Protecting Groups) (Book).

Handbook of Pharmaceutical Salts: Properties, Selection, and Use, 2$^{nd}$ Revised Edition, P.H. Stahl and C.G. Wermuch, Eds., © 2011 Wiley-VCH, an imprint of John Wiley & Sons, Inc. (Hoboken, New Jersey), ISBN 978-3-90639-051-2 (Book).
Hoyle, Charles E.; Bowman, Christopher N. (2010) "Thiol-Ene Click Chemistry," *Angewandte Chemie International Edition* 49(9): 1540 -1573.
Johnson, J. A.; Baskin, J. M.; Bertozzi, C. R.; Koberstein, J. T.; Turro, N. J. (2008) "Copper-free click chemistry for the in situ crosslinking of photodegradable star polymers," *Chem. Commun.* 3064-3066.
Kocienski, Philip J. "Protecting Groups," (Georg Thieme Verlag Stuttgart, New York, 1994) (Book).
Kolb, H. C.; Finn, M. G.; Sharpless, K.B. (2001) "Click Chemistry: Diverse Chemical Function from a Few Good Reactions," *Angewandte Chemie International Edition* 40(11):2004-2021.
Ni, Mitsuda, Kashiwagi, Igawa, and Tomooka (2015) "Heteroatom-embedded Medium-Sized Cycloalkynes: Concise Synthesis, Structural Analysis, and Reactions," *Angewandte Chemie International* 54(4):1190-1194.

(Continued)

*Primary Examiner* — Noble E Jarrell
(74) *Attorney, Agent, or Firm* — Joseph T. Leone, Esq.; DeWitt LLP

(57) ABSTRACT

Compounds of Formula I:

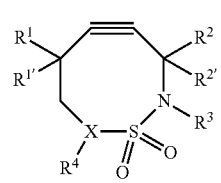

(Formula I)

wherein:

$R^1$ and $R^{1'}$ are independently selected from hydrogen, halogen, $C_1$-to-$C_{12}$ linear or branched hydroxyalkyl, $C_1$-to-$C_{12}$ linear or branched halo-alkyl, carboxy, carboxyalkyl, amido, N-alkylamido, N,N-dialkylamido, carbamoyloxy, N-alkylcarbamoyloxy, and N,N-dialkylcarbamoyloxy, provided that that $R^1$ and $R^{1'}$ are not simultaneously hydrogen; $R^2$ and $R^{2'}$ hydrogen, halogen, $C_1$-to-$C_{12}$ linear or branched hydroxyalkyl, $C_1$-to-$C_{12}$ linear or branched halo-alkyl, carboxy, carboxyalkyl, amido, N-alkylamido, N,N-dialkylamido, carbamoyloxy, N-alkylcarbamoyloxy, and N,N-dialkylcarbamoyloxy, provided that that $R^2$ and $R^{2'}$ are not simultaneously hydrogen; $R^3$ is selected from hydrogen, $C_1$ to $C_{12}$ linear or branched alkyl, and nitrogen protecting groups; X is oxygen or nitrogen; when X is oxygen, $R^4$ is absent; and when X is nitrogen, $R^4$ is selected from H, $C_1$-to-$C_{12}$ linear or branched alkyl, and nitrogen protecting groups.

23 Claims, 5 Drawing Sheets

(56) References Cited

PUBLICATIONS

Sletten, E. M.; Bertozzi, C. R. (2008) "A Hydrophilic Azacyclooctyne for Cu-Free Click Chemistry," *Org. Lett.* 10:3097-3099.

Spiteri, Christian; Moses, John E. (2010) "Copper-Catalyzed Azide-Alkyne Cyclo addition: Regioselective Synthesis of 1,4,5-Trisubstituted 1,2,3-Triazoles," *Angewandte Chemie International Edition* 49(1):31-33.

* cited by examiner

*Previous work: electronic effects on azide–alkyne cycloadditions*

A

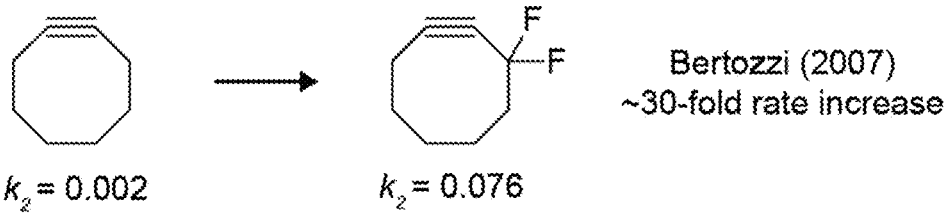

Bertozzi (2007)
~30-fold rate increase $k_2 = 0.002$     $k_2 = 0.076$

B

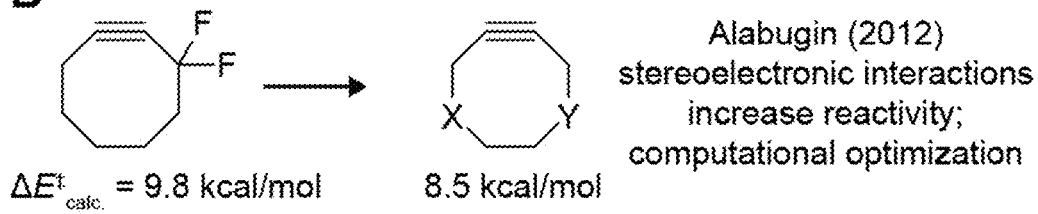

Alabugin (2012)
stereoelectronic interactions
increase reactivity;
computational optimization $\Delta E^{\ddagger}_{calc.} = 9.8$ kcal/mol     8.5 kcal/mol

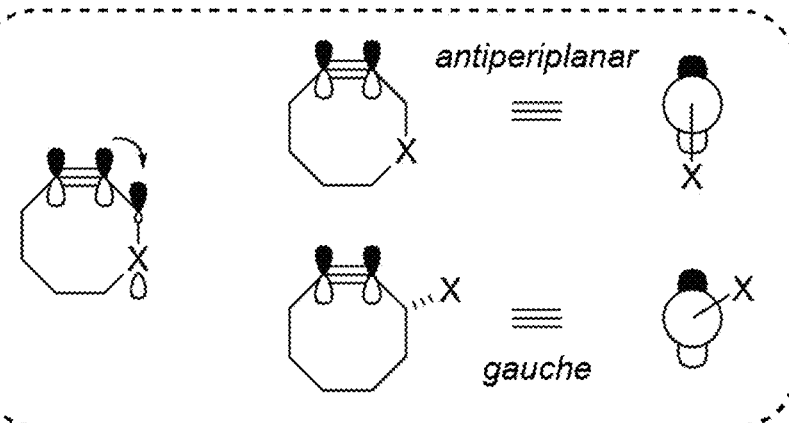

C

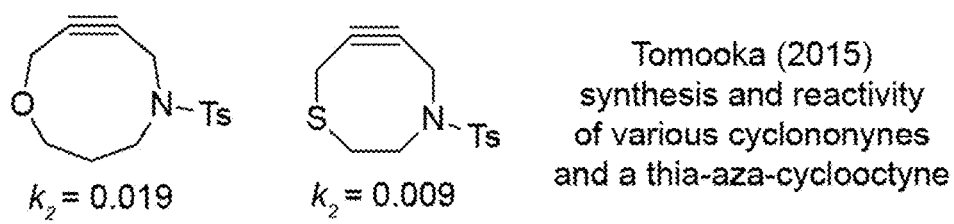

Tomooka (2015)
synthesis and reactivity
of various cyclononynes
and a thia-aza-cyclooctyne $k_2 = 0.019$     $k_2 = 0.009$

*This work:*

D 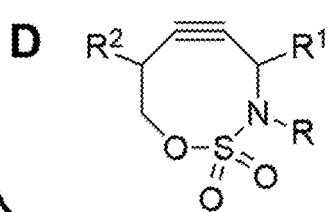

– unexpectedly large effect of a single propargylic heteroatom
– increased effects in cycloadditions of diazoacetamides over azides
– ease of synthesis and manipulation

FIG. 1

ELECTRONICALLY ACTIVATED STRAINED ALKYNES

CROSS-REFERENCE TO RELATED APPLICATIONS

This is a continuation-in-part of application Ser. No. 15/873,984, filed Jan. 18, 2018, now U.S. Pat. No. 10,233,162, issued Mar. 19, 2019, which claims priority to provisional application Ser. No. 62/447,466, filed 18 Jan. 2017, both of which are incorporated herein by reference.

FEDERAL FUNDING STATEMENT

This invention was made with government support under GM111412 awarded by the National Institutes of Health. The government has certain rights in the invention.

BACKGROUND

The difficulty of synthesizing a diverse array of complex molecules from readily available precursors has led to the development of many elegant and highly specific transformations in efforts to reach desired targets. An alternate approach to generating many specialized transformations focuses instead on using a small pool of highly efficient reactions. The idea of "click chemistry" mimics nature's modular usage of heteroatom linkages to afford a wide variety of macromolecular scaffolds. See H. C. Kolb; M. G. Finn; K. B. Sharpless (2001) "Click Chemistry: Diverse Chemical Function from a Few Good Reactions," *Angewandte Chemie International Edition* 40 (11):2004-2021. While it is unlikely this approach would completely supplant the traditional strategies of molecular synthesis, the use of "click chemistry" has had notable applications and widespread use. See, for example, R. A. Evans (2007) "The Rise of Azide-Alkyne 1,3-Dipolar 'Click' Cycloaddition and its Application to Polymer Science and Surface Modification," *Australian Journal of Chemistry* 60 (6):384-395; Spiteri, Christian; Moses, John E. (2010) "Copper-Catalyzed Azide-Alkyne Cycloaddition: Regioselective Synthesis of 1,4,5-Trisubstituted 1,2,3-Triazoles," *Angewandte Chemie International Edition* 49 (1):31-33; and Hoyle, Charles E.; Bowman, Christopher N. (2010) "Thiol-Ene Click Chemistry," *Angewandte Chemie International Edition* 49 (9):1540-1573.

In the design and optimization of reactions used in this manner, basic principles of chemical reactivity must be utilized. Whether a cascade reaction leads to a complex natural product (for example, a specialized Diels-Alder cycloadditions employed by Boger) or a simple $S_N2$ displacement, understanding how to manipulate weak bonds in starting compounds and transform them into strong bonds in the products requires the presence of a "driving force." When the inherent energy profile is not favorable for the desired reaction to go to completion, an extra 'push' is often provided by a catalyst. This is the case for arguably the most efficient "click" reaction, the copper-catalyzed azide-alkyne cycloaddition (CuAAC). See, for example, Castro, Rodríguez and Albericio (2016) "CuAAC: An Efficient Click Chemistry Reaction on Solid Phase," *ACS Comb. Sci.* 18 (1):1-14. While CuAAC is undoubtedly an incredibly valuable transformation with broad applications, limitations do exist which are often linked to the requirement for this catalyst.

In place of a catalyst, one highly effective strategy to promote reactivity has been the use of the release of strain energy. See FIG. 1, panels A, B, and C. However, incorporating strained alkynes into the starting compounds can increase reactivity of the alkyne bond to the point that is extremely difficult to isolate the starting compound. In fact, early attempts required a cycloaddition reaction to trap the intermediate cyclooctynes in order to prove their generation in situ. Since these early reports of strain as a method to increase reactivity, there has been intense interest in these unique molecules that was further renewed when strain was applied to azide-alkyne cycloadditions (strain-promoted azide-alkyne cycloadditions, SPAAC). See, for example, Baskin, J. M.; Bertozzi, C. R. (2007) "Bioorthogonal Click Chemistry: Covalent Labeling in Living Systems," *QSAR Comb. Sci.* 26:1211-1219; Codelli, J. A.; Baskin, J. M.; Agard, N. J.; Bertozzi, C. R. (2008) "Second-Generation Difluorinated Cyclooctynes for Copper-Free Click Chemistry," *J. Am. Chem. Soc.* 130:11486-11493; Johnson, J. A.; Baskin, J. M.; Bertozzi, C. R.; Koberstein, J. T.; Turro, N. J. (2008) "Copper-free click chemistry for the in situ cross-linking of photodegradable star polymers," *Chem. Commun.* 3064-3066; and Sletten, E. M.; Bertozzi, C. R. (2008) "A Hydrophilic Azacyclooctyne for Cu-Free Click Chemistry," *Org. Lett.* 10:3097-3099.

The strain energy present in various cycloalkynes was used by Bertozzi and co-workers, supra, to sidestep the cytotoxicity associated with CuAAC by eliminating the need for copper catalysts, which proved problematic when attempting to use Huisgen 1,3-dipolar reactions in vivo. Since this initial report, new cyclic alkynes have been reported, with properties expanding the utility of this chemistry. These types of reactions are used in various fields, including biological labeling, the synthesis of specialized polymers and ligands, and the generation of libraries of medicinally relevant compounds.

The value of cycloalkynes is due, in part, to their fast rates of reaction. As a result, several strategies have been explored to increase their reactivity in a predictable and controllable manner. The most common approach involves "ring strain activation," where cyclopropanes, aryl groups or other sites of unsaturation are introduced into the molecule providing for rate enhancement of >2 orders of magnitude. Examples include the compounds known by their trivial names as bicyclo[6.1.0]nonyne ("BCN"), dibenzocyclooctynone ("DIBONE"), and dibenzoazacyclooctyne ("DIBAC"):

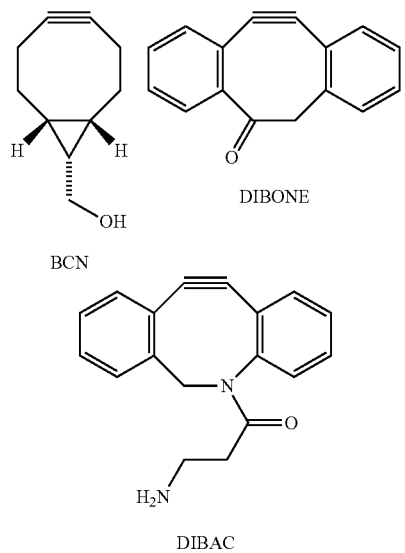

However, this strategy can be problematic, as these changes result in inherent destabilization of the ring. Cycloalkynes activated primarily by increased strain may become sensitive to heat or light, they require harsh conditions to prepare, and typically have a very short shelf life.

A different tactic to increase reactivity is achieved by manipulation of the desired reaction's transition state through electronic stabilization, in addition to the typical ring strain. See FIG. 1, panels A and B. This allows for an increase in reactivity over alkynes which rely solely on strain activation without sacrificing stability of the alkyne. In addition to raising the reactivity of the alkyne, combining electronic activation with strain offers the possibility of tuning each alkyne to a distinct coupling partner. Theoretically, this should yield alkynes with both fast reaction rates and selective reactivity.

The most successful previous efforts to combine strain and electronic effects take advantage of the increased reactivity provided by electronegative atoms at the propargylic position. Again, see FIG. 1 at panels A and B. It has been shown that rate enhancements which stem from hyperconjugative $\pi \rightarrow \sigma^*_{C-X}$ interactions are especially important contributors in the transition state (TS). When σ-acceptors are also contained within the cyclic framework, they allow for strengthened hyper-conjugative ($\pi \rightarrow \sigma^*_{C-X}$) interactions relative to systems containing exocyclic σ-acceptors. This is a result of the orientation of the endocyclic propargylic atom(s), which lie antiperiplanar relative to the new bonds being formed. See FIG. 1, panel B. When the σ-acceptor is located in an endocyclic orientation, it is already positioned appropriately for maximal electronic interaction in the transition state. This is in contrast to the gauche orientation noted when the propargylic σ-acceptors are exocyclic, as the propargylic C—C bond of the ring precludes them from adopting the ideal antiperiplanar geometry. Tomooka and co-workers recently synthesized medium-sized cycloalkynes with heteroatoms embedded at the propargylic positions that enable cycloaddition rates faster than those of cyclooctyne ("OCT") and monofluorinated cyclooctyne ("MOFO"), but do not yet surpass those of difluorocyclooctyne (DIFO). See Ni, Mitsuda, Kashiwagi, Igawa, and Tomooka (2015) "Heteroatom-embedded Medium-Sized Cycloalkynes: Concise Synthesis, Structural Analysis, and Reactions," *Angewandte Chemie International* 54 (4):1190-1194.

Although many impressive strained alkynes have been reported, the existing chemistry remains far from optimal. There is an ongoing and unmet need for new strained cycloalkynes that offer ease and flexibility in synthesis, chemoselectivity, and reduced lipophilicity.

SUMMARY

Disclosed herein is a new class of cycloalkynes which incorporate heteroatoms into the ring. Also disclosed are method to make these novel cycloalkynes, and their use as reactants in 1,3-dipolar cycloaddition reactions. This method to make the cycloalkynes is very flexible and can be used to make a host of modifications to the basic structure. The resulting cycloalkynes are thus "tunable" with respect to their rate of reaction and their chemoselectivity against both unwanted side reactions and the potential for selective reactivity between different types of dipoles (for example, selective reactivity with azide dipoles versus diazoacetamide dipoles).

Disclosed are compounds of Formula I:

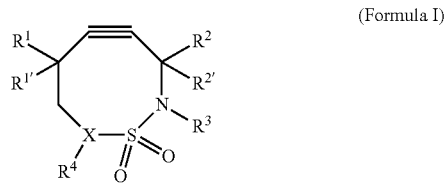

(Formula I)

wherein:

$R^1$ and $R^{1'}$ are independently selected from hydrogen, halogen, $C_1$-to-$C_{12}$ linear or branched hydroxyalkyl, $C_1$-to-$C_{12}$ linear or branched halo-alkyl, carboxy, carboxyalkyl, amido, N-alkylamido, N,N-dialkylamido, carbamoyloxy, N-alkylcarbamoyloxy, and N,N-dialkylcarbamoyloxy, provided that that $R^1$ and $R^{1'}$ are not simultaneously hydrogen;

$R^2$ and $R^{2'}$ hydrogen, halogen, $C_1$-to-$C_{12}$ linear or branched hydroxyalkyl, $C_1$-to-$C_{12}$ linear or branched halo-alkyl, carboxy, carboxyalkyl, amido, N-alkylamido, N,N-dialkylamido, carbamoyloxy, N-alkylcarbamoyloxy, and N,N-dialkylcarbamoyloxy, provided that that $R^2$ and $R^{2'}$ are not simultaneously hydrogen;

$R^3$ is selected from hydrogen, $C_1$ to $C_{12}$ linear or branched alkyl, and nitrogen protecting groups;

X is oxygen or nitrogen;

when X is oxygen, $R^4$ is absent; and when X is nitrogen, $R^4$ is selected from H, $C_1$-to-$C_{12}$ linear or branched alkyl, and nitrogen protecting groups.

Also disclosed herein is a method of forming chemical bonds. The method comprises reacting a first compound as recited in the preceding paragraphs with a second compound comprising a 1,3-dipole in a 1,3-cycloaddition reaction.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite article "a," when applied to a claimed element, means "one or more," unless explicitly stated to the contrary.

All combinations of method or process steps as used herein can be performed in any order, unless otherwise specified or clearly implied to the contrary by the context in which the referenced combination is made.

The methods, compounds, and compositions of the present invention can comprise, consist of, or consist essentially of the essential elements and limitations of the invention as described herein, as well as any additional or optional ingredients, components, or limitations described herein or otherwise useful in synthetic organic chemistry.

BRIEF DESCRIPTION OF THE DRAWINGS

FIG. 1 is a series of illustrations depicting various types of prior art SPAAC-type reactions (panels A, B, and C) as contrasted to the present process (panel D). Panels A, B, and C note the electronic effects on rate and selectivity of the various types of strain-promoted 1,3-dipolar-alkyne cycloadditions.

DETAILED DESCRIPTION

Abbreviations and Definitions

Figure 2:
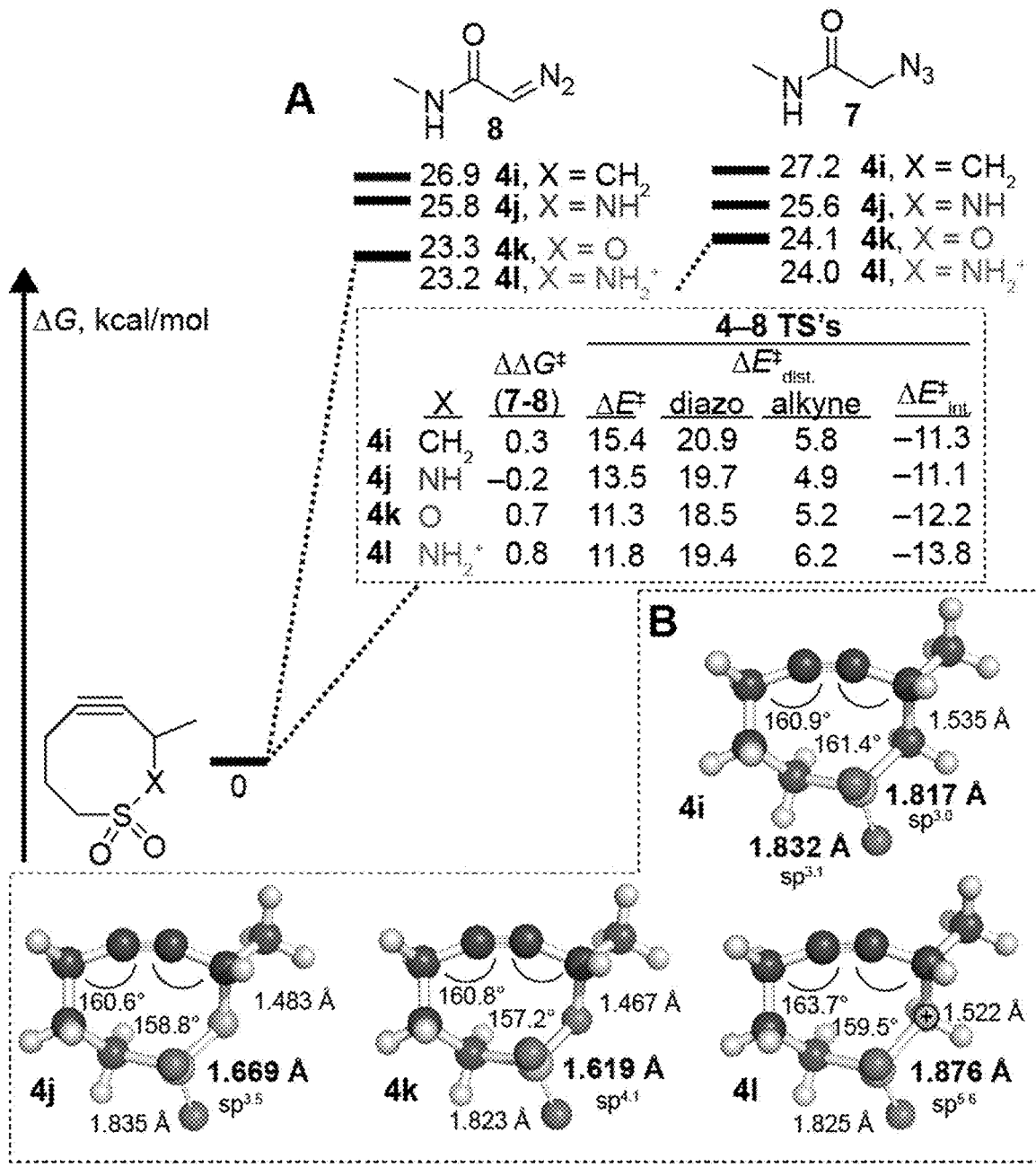
FIG. 2 is an illustration depicting, in panel A, the free energies of activation (kcal/mol) of the lowest energy transition states for each cycloadditions of diazo- and azidoacetamides reacting with alkynes containing various propargylic substituents. Geometries optimized at the M06-2X/6-311+G(d,p) level of theory with an IEFPCM solvent model for water (radii=UFF). Inset: Distortion/interaction analysis for cycloadditions of diazoacetamide. Panel B depicts starting alkyne geometries with selected bond lengths given in Å and angles in degrees. Hybridizations obtained from NBO analysis are given for sulfur bonding orbitals in S—X bonds. Black=carbon; white=hydrogen; blue=nitrogen; red=oxygen; yellow=sulfur.

BCN=bicyclo[6.1.0]nonyne.
CuAAC=copper-catalyzed azide-alkyne cycloaddition.
DIBAC=dibenzoazacyclooctyne.
DIBONE=dibenzocyclooctynone.
Halogen=chlorine, fluorine, bromine, and iodine.
IEFPCM=integral equation formalism variant of the polarizable continuum model.
NBO=natural bond orbital.
OCT=cyclooctyne. SNO-OCT refers to heterocyclic cyclooctynes having sulfur, nitrogen, and oxygen heteroatoms.
SPAAC=strain-promoted alkyne-azide cyclization.
TBAF=tetra-n-butylammonium fluoride
TS=transition state.
UFF=universal force field.

In the present description, unless otherwise indicated, terms such as "compounds of the invention" and "compounds disclosed herein" embrace the compounds in salt form as well as in free acid or base form (as the case may be) and also when the compounds are attached to a solid phase. Where a basic substituent such as an amine substituent is present, the salt form may be an acid addition salt, for example a dihydrochloride. Conversely, where an acidic substituent is present, the salt form may be a base addition salt. Salts include, without limitation, acid addition salts such as those derived from mineral acids and organic acids, explicitly including hydrohalides, e.g., hydrochlorides and hydrobromides, sulfates, phosphates, nitrates, sulfamates, acetates, citrates, lactates, tartrates, malonates, oxalates, salicylates, propionates, succinates, fumarates, maleates, methylene bis-b-hydroxynaphthoates, gentisates, isethionates, di-p-toluoyltartrates, methane sulfonates, ethanesulfonates, benzenesulfonates, p-toluenesulfonates, cyclohexylsulfamates, quinates, and the like. Base addition salts include those derived from alkali or alkaline earth metal bases or conventional organic bases, such as triethylamine, pyridine, piperidine, morpholine, N-methylmorpholine, and the like. Other suitable salts are found in, for example, "Handbook of Pharmaceutical Salts: Properties, Selection, and Use, $2^{nd}$ Revised Edition," P. H. Stahl and C. G. Wermuch, Eds., © 2011 Wiley-VCH, an imprint of John Wiley & Sons, Inc. (Hoboken, N.J.), ISBN 978-3-90639-051-2, which is incorporated herein by reference.

The invention includes the compounds of the invention in pure isomeric form, e.g., consisting of at least 90%, preferably at least 95% of a single isomeric form, as well as mixtures of these forms. The compounds of the invention may also be in the form of individual enantiomers or may be in the form of racemates or diastereoisomeric mixtures or any other mixture of the possible isomers.

A "protecting group" is any chemical moiety capable of selective addition to and removal from a reactive site to allow manipulation of a chemical entity at sites other than the reactive site. Many protecting groups are known in the art. A large number of protecting groups and corresponding chemical cleavage reactions are described in "Greene's Protective Groups in Organic Synthesis," ISBN-13: 978-1118057483, ©2014, John Wiley & Sons, Inc. The term "nitrogen protecting group" is specifically directed to protecting groups that are capable of selective addition to and removal from a reactive nitrogen atom in a molecule (to allow manipulation of a chemical entity at sites other than the protected, reactive nitrogen atom). Greene describes many nitrogen protecting groups, for example, amide-forming groups. In particular, see Chapter 1, Protecting Groups: An Overview, Chapter 2, Hydroxyl Protecting Groups, Chapter 4, Carboxyl Protecting Groups, and Chapter 5, Carbonyl Protecting Groups. For additional information on protecting groups, see also Kocienski, Philip J. "Protecting Groups," (Georg Thieme Verlag Stuttgart, New York, 1994), which is incorporated herein by reference. Typical nitrogen protecting groups described in Greene include benzyl ethers, silyl ethers, esters including sulfonic acid esters, carbonates, sulfates, and sulfonates. For example, suitable nitrogen protecting groups include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate(mesitoate)); carbonates (methyl, 9-fluorenylmethyl, ethyl, 2,2,2-trichloroethyl, 2-(trimethylsilyl) ethyl, 2-(phenylsulfonyl)ethyl, 2-(triphenylphosphonio) ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl) benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-poly-benzoate, α-naphthoate, nitrate, alkyl N,N,N',N'-tetramethyl-phosphorodiamidate, n-phenylcarbamate, borate, 2,4-dinitrophenylsulfenate); or sulfonates (methanesulfonate(mesylate), benzenesulfonate, benzylsulfonate, tosylate, or triflate).

The more common of the amine-protecting groups have trivial abbreviations that are widely used in the literature and include: carbobenzyloxy (Cbz) group (removed by hydrogenolysis), p-methoxybenzyl carbonyl (Moz or MeOZ) group (removed by hydrogenolysis), tert-butyloxycarbonyl (BOC) group (common in solid phase peptide synthesis; removed by concentrated strong acid (such as HCl or CF$_3$COOH), or by heating to >80° C., 9-fluorenylmethyloxycarbonyl (FMOC) group (also common in solid phase peptide synthesis; removed by base, such as piperidine), acetyl (Ac) group (removed by treatment with a base), benzoyl (Bz) group (removed by treatment with a base), benzyl (Bn) group (removed by hydrogenolysis), carbamate group (removed by acid and mild heating), p-methoxybenzyl (PMB) (removed by hydrogenolysis), 3,4-dimethoxybenzyl (DMPM) (removed by hydrogenolysis), p-methoxyphenyl (PMP) group (removed by ammonium cerium(IV) nitrate (CAN)), tosyl (Ts) group (removed by concentrated acid and strong reducing agents), sulfonamide groups (Nosyl & Nps; removed by samarium iodide, tributyltin hydride.

As used herein, the phrase "1,3-dipole," as in "a compound comprising a 1,3-dipole", means dipolar compounds having delocalized electrons and a separation of charge over three atoms and capable of being a reactant in a 1,3-dipolar cycloaddition reaction. A non-exclusive list of compounds comprising a 1,3-dipole includes azides (R—N$_3$), ozone (O$_3$), nitro compounds (R—NO$_2$), diazo compounds (R$_2$—C=N=N), certain oxides (such as, but not limited to azoxide compounds (RN(O)NR) carbonyl oxides (Criegee zwitterions), nitrile oxides (RCN—O), nitrous oxide (N$_2$O), and nitrones (R$_2$CN(R)O), carboynyl oxide, certain imines (such as azomethine imine, nitrilimines (RCN—NR, analogous to nitrile oxide) and carbonyl imines), and certain ylides (including azomethine ylide, nitrile ylide (RCNCR'$_2$), carbonyl ylide, and thiosulfines (R$_2$CSS)).

1,3-dipoles may also be organized by structure as nitrogen-centered or oxygen-centered allyl-type or propargyl-allenyl-type. Nitrogen-centered, allyl-type 1,3-dipoles include, but are not limited to:

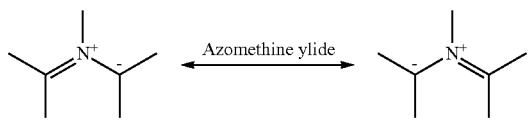
Azomethine ylide

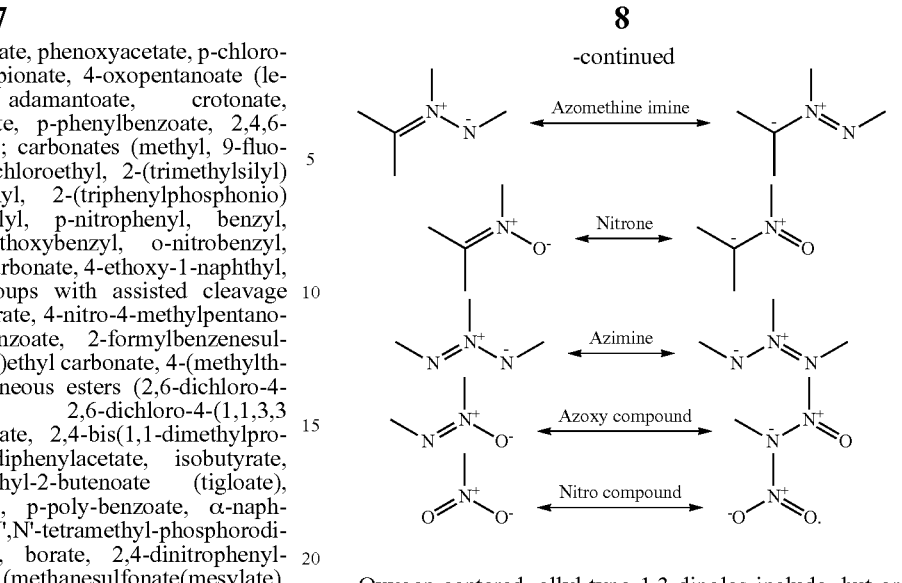

Oxygen-centered, allyl-type 1,3-dipoles include, but are not limited to:

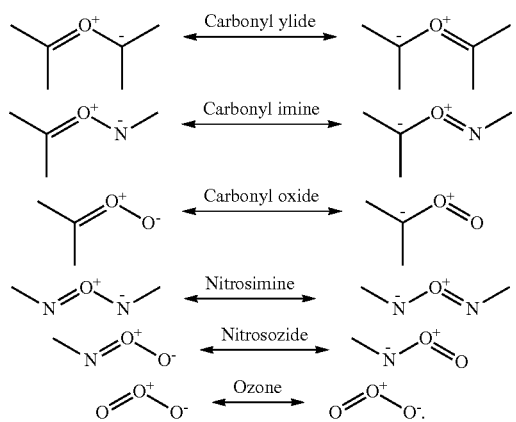

Propargyl-allenyl-type 1,3-dipoles include, but are not limited to, nitrilium betaines such as

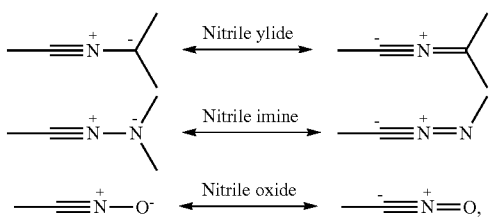

as well as diazonium betaines, such as

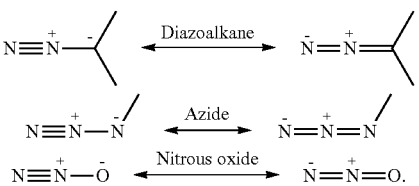

Synthesis of Strained Cycloalkynes

One of the ongoing challenges when using conventional strained cycloalkynes is their very difficult synthesis. Prior art syntheses are lengthy and offer few opportunities for derivatization. In contrast, the present process begins with readily accessible silylated allenes (1, Scheme 1). The presence of the silyl group directs the regioselectivity of the aziridination to the distal allene to yield an endocyclic methylene aziridine 2. In prior art syntheses, the remaining alkene underwent diastereo selective epoxidation, followed by rapid rearrangement, to form azetidin-3-ones represented by 3. However, the inventive process treats 2 with TBAF, which triggers elimination of the silyl group, followed by ring-opening of the aziridine, to yield the novel strained alkyne 4 with heteroatoms incorporated into the ring at strategic positions.

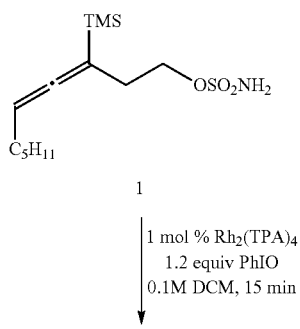

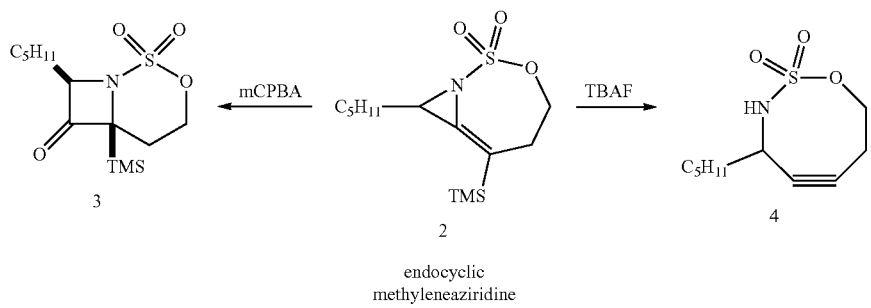

The scope of the reaction is illustrated in Table 1. Analogs of the allenic precursor 1 allow for varied alkyl substitution at the C1 and C4 positions. This allowed for an investigation of the effects of steric bulk, as well as a demonstration of the ability to include tethered functional groups. The propargyl nitrogen can be protected, which permits the electronic properties and strain experienced by the alkyne to be varied or "tuned." Additionally, the homopropargylic oxygen atom can be replaced with a nitrogen atom by using a homoallenic sulfamide precursor. The flexibility of this scaffold allows for tuning of the strained alkyne. The synthetic approach can also be used to optimize the reactivity of the alkyne for its desired coupling partner (vide infra). Overall, the synthesis is rapid, high yielding, and easily diversified. It is also notable that these strained alkynes are easily isolable solids which are stable to heat and light, as well as to both acidic and basic reaction conditions. The stability of the inventive cyclooctynes in the presence of biologically relevant functional groups, including a free thiol, was assessed by stirring the alkyne with glutathione in a PBS buffered solution for 24 h. No reaction was observed.

TABLE 1

Scope of cycloalkyne formation and reactivity with benzyl azide.

| entry | substrate | product | yield (%) | 1,3-dipolar cycloaddition | | |
|---|---|---|---|---|---|---|
| | | | | yield (%) | $k_2$ | $k_{rel.}$ |
| 1 | 1a | 4a | XX | XX | 0.066 | 2.6 |
| 2 | 1b | 4b | XX | XX | 0.025 | 1.0 |
| 3 | 1c | 4c | XX | XX | 0.0040 | 0.16 |
| 4 | 1d | 4d | XX | XX | 0.037 | 1.5 |
| 5 | 1e | 4e | XX | XX | 0.042 | 1.7 |

TABLE 1-continued

Scope of cycloalkyne formation and reactivity with benzyl azide.

| entry | substrate | product | yield (%) | 1,3-dipolar cycloaddition yield (%) | $k_2$ | $k_{rel.}$ |
|---|---|---|---|---|---|---|
| 6 | 1f | 4f | XX | XX | XX | XX |
| 7 | 1g | 4g | XX | XX | 0.047 | 1.9 |
| 8 | 1h | 4h | XX | XX | 0.0014 | 0.056 |

Reactivity of Strained Cycloalkynes with Benzyl Azide

The reactivity of the novel strained alkyne derivatives disclosed herein were first assessed using benzyl azide 5 as a model substrate (Table 1, model reaction at top). In acetonitrile at ambient temperatures, the second order rate constant for substrate 4b ($C_5H_{11}$) was found to be $2.5 \times 10^{-2}$ $M^{-1}s^{-1}$. When steric hindrance was increased by placing the more bulky isopropyl group at C1, the rate of the reaction slowed to a sixth of that of substrate 4c. Conversely, decreasing the steric bulk in substrate 4a ($R^1$=Me) showed dramatically increased rate—the reaction proceeds 2.6 times faster than alkyne 4b. The effects of the heteroatoms in the ring were similarly pronounced. When the propargyl nitrogen was protected with a Boc group, the rate slowed slightly (4e). For Me-substituted substrates 4a and 4d, the rates slowed to roughly half their unprotected values. While a more electron-poor nitrogen heteroatom is expected to result in a stronger electronic effect and an expected increase in reaction rate, the conflicting effects of bond lengthening and steric repulsion between the Boc and $R^1$ groups overrides any benefit and results in a net slowing of rate. Similarly, when the homopropargylic oxygen atom was replaced with a Boc-protected nitrogen atom, the rate fell dramatically to an eighteenth of that of the sulfamate (4f). The fastest substrate, 1a, compares favorably to other reported strained alkynes. It is faster than OCT, the exocyclic heteroatom-activated MOFO, and the endocyclic heteroatom-activated alkynes reported by Toomoka et al., supra. The reaction rate of 1a is surpassed only slightly by DIFO. See Table 2 for comparison.

TABLE 2

Rate comparisons of common cycloalkynes with diazoazetamide and azidoacetamide in $CD_3CN$ ($^aCD_3CN:D_2O = 1:1$)

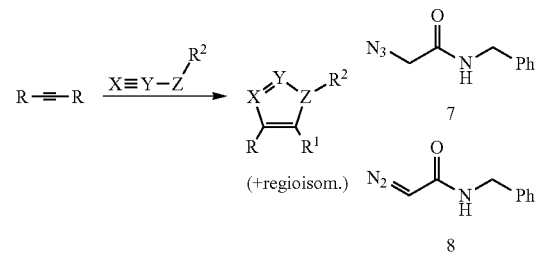

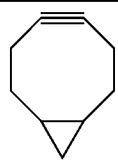

BCN
$k_2(7:8)$: 0.73

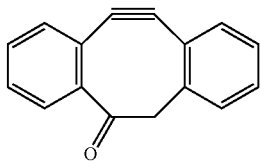 [SMILES: O=C1Cc2ccccc2C#Cc2ccccc21]

DIBONE
2.1

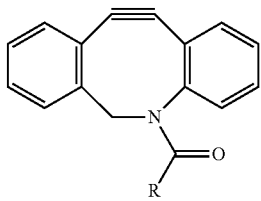

DIBAC
2.0, 6.5$^a$

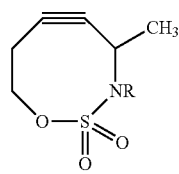

4a, R = H: 3.0, 8.5$^a$
4d, R = Boc: 5.0

Thus, the novel cyclooctynes described herein are sufficiently reactive for a large number of "click chemistry" applications. Furthermore, the inventive cyclooctynes are afforded in far fewer steps and higher yields than DIFO, providing for a much more accessible "click" reagent.

Designing Cyclooctynes with Increased Chemoselectivity

Previous work directed towards the reactions of cyclooctynes has focused heavily on azide-alkyne cycloadditions. (See the above-noted references.) While this has been a fruitful area with many useful applications, cycloalkynes will partner with other substrates. Nitrones, nitrile oxides, and diazo compounds have all been demonstrated to undergo rapid reactions with strained alkynes without the need for transition metal catalysts. By looking beyond azides for coupling partners, new orthogonal labeling systems are accessible for providing tandem chemoselective transformations in a cellular context.

For these exploratory studies, diazoacetamide 8 (Table 3) and azidoacetamide 7 were chosen because of the increased nucleophilicity of 8 as compared to azide 7 and its ability to survive cellular metabolism. When comparing rate differences with diazoacetamide 8 and azidoacetamide 7 for common cycloalkynes, DIBAC reacted~5-times faster with the diazoacetamide than the analogous azide in 1:1 $CD_3CN:D_2O$. This rate difference shows promise that the right balance of strain and electronic activation can be reached to provide for robust reagents displaying relatively rapid reaction kinetics. At the same time, these compounds provide for complete selectivity that is as of yet lacking in cyclooctynes. It was hypothesized by the present inventors that properly positioned heteroatoms in sulfamate-derived cyclooctynes would lead to an increase in diazo-selective reactivity over azides, thus enabling orthogonal bioconjugation techniques. It was found that under the same reaction conditions, the gap in reactivity for cycloalkyne 4 was even larger than that of DIBAC.

TABLE 3

Experimental rate constants and calculated activation energies and free energies (kcal/mol) for the lowest energy transition states for cycloadditions of diazo- and azidoacetamide reacting with alkynes 4a and 4d.

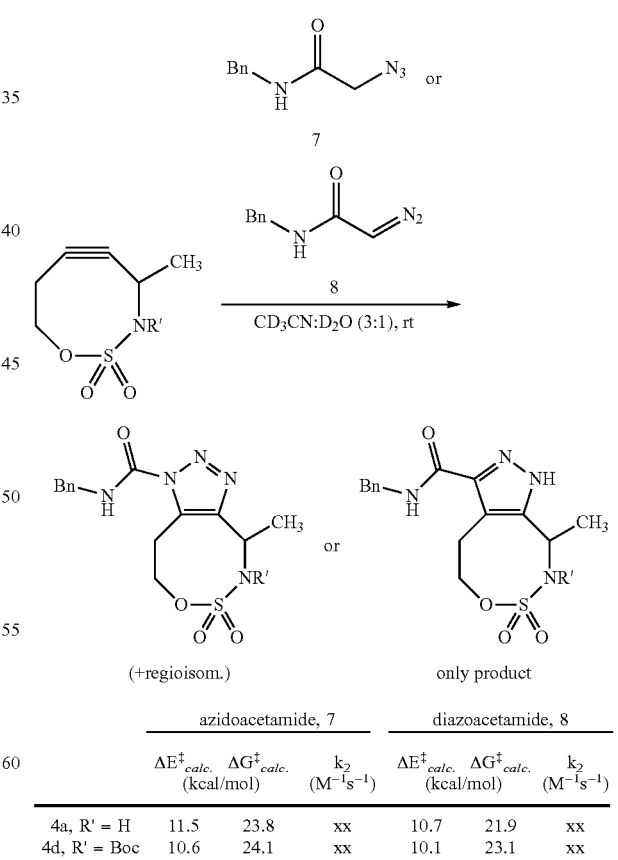

|  | azidoacetamide, 7 | | | diazoacetamide, 8 | | |
| --- | --- | --- | --- | --- | --- | --- |
|  | $\Delta E^{\ddagger}_{calc.}$ (kcal/mol) | $\Delta G^{\ddagger}_{calc.}$ (kcal/mol) | $k_2$ ($M^{-1}s^{-1}$) | $\Delta E^{\ddagger}_{calc.}$ (kcal/mol) | $\Delta G^{\ddagger}_{calc.}$ (kcal/mol) | $k_2$ ($M^{-1}s^{-1}$) |
| 4a, R' = H | 11.5 | 23.8 | xx | 10.7 | 21.9 | xx |
| 4d, R' = Boc | 10.6 | 24.1 | xx | 10.1 | 23.1 | xx |

Geometries were optimized at the M06-2X/6-311 + G(d,p) level of theory using an IEFPCM solvent model for water (radii = UFF).
Bn was replaced with Me for simplicity in computations.

The effects of the various heteroatoms on this increased chemoselectivity were investigated computationally. Reaction of the standard substrate 4 (Table 3) with diazoacetamide 8 was found experimentally to be about an order of magnitude faster than reaction with azidoacetamide 7. This observation suggests a $\Delta\Delta G^\ddagger$ of ~1.3 kcal/mol, while computations predicted $\Delta\Delta G^\ddagger$ and $\Delta\Delta E^\ddagger$ values of 1.9 and 0.8 kcal/mol, respectively, for the unsubstituted sulfamates 4a. Computations indicated that Boc-substitution decreases the $\Delta\Delta E^\ddagger$ for reaction of both the diazoacetamide and azidoacetimide as the nitrogen becomes a better σ-acceptor. In contrast, the $\Delta\Delta G^\ddagger$ is expected to increase, likely due to increased steric repulsion from the bulky Boc-group. This difference in rate provides ~9:1 selectivity in competition experiments involving 1:1:1 mixtures of diazoacetamide (7):azidoacetamide (8):alkyne (4d, 4e). Efforts to improve the selectivity for reaction with 1 were undertaken by examining the effects of both propargylic and homopropargylic heteroatoms in 4.

In the most closely related system, the cyclooctyne previously reported by Toomoka (FIG. 1, panel C), an N-tosyl and thioether linker occupy each of the endocyclic propargylic sites. The compounds and methods disclosed herein differ in two key ways. First, only one of the endocyclic propargylic positions is occupied by a heteroatom (nitrogen; see FIG. 1, panel D) and second, the nature of the endocyclic sulfamate replaces two carbon atoms of the ring with heteroatoms (oxygen and sulfur). Based on these features, it is reasonable to expect slower rates with compounds according to the present invention (such as 4; see Table 1) as compared to Toomoka's alkyne as shown in FIG. 1, panel C. This is because the inventive compounds experience hyperconjugative assistance from only one propargylic heteroatom. However, that's not the case. Experimental results showed enhanced reactivity of the present compounds as compared to Toomoka's. This was a very surprising and unexpected outcome.

Computational Studies of Cycloalkynes

Introduction of a sulfonyl group into an all-carbon cyclooctyne ring relieves ring strain as a result of long C—S bonds and an increase in the linearization of alkyne angles (~158/159° to ~161/161°). In addition, the homopropargylic sulfonyl generates a more polar transition state in a cycloaddition reaction, as determined by NBO charges on the reacting partners. (Data not shown.) This is due to inductive effects, as well as double hyperconjugation through the exocyclic propargylic C—C bonds. This renders the $\Delta\Delta G^\ddagger$ upon sulfonyl incorporation (4i) smaller for the diazoacetamide than for the azide. However, the way in which the two heteroatoms adjacent to the sulfonyl group (N and O in the case of the sulfamate of 4a) interact synergistically to increase the reactivity of the inventive cycloalkynes was not clear. To address this issue, computational studies were undertaken.

Both the observed chemo- and regioselectivity were recapitulated by calculated values, where both dipoles favored approaching "anti" to the propargylic nitrogen and methyl group. To assess the effect of the sulfonyl group on previously reported $\pi\rightarrow\sigma^*$C—X interactions, a series of compounds differing in the electron-accepting ability of the propargylic σ bond were examined (X=NH, O, $NH_2^+$; see FIG. 2, panel A). All three heteroatoms decrease the barrier relative to compound 4i, containing only an $SO_2$ group. Additionally, increased selectivity for cycloadditions of the diazoacetamide is predicted (larger $\Delta\Delta G^\ddagger$ values) for compounds 4k and 4l (X=O and $NH_2^+$, respectively).

Decreased activation energies were expected as the electron-acceptor abilities of the X group were increased, but this trend was not followed. The reaction of diazoacetamide 8 and 4k displayed a lower activation energy (and a nearly identical free energy of activation) than the reaction with 4l (see FIG. 2). Without being constrained to a given mechanism, this is thought to result from an increased S—N bond length upon protonation of the nitrogen, a direct effect of Bent's rule. (Bent, H. A. (1961) "An appraisal of valence-bond structures and hybridization in compounds of the first-row elements," *Chem. Rev.* 61 (3):275-311.) As the electronegativity of the propargylic atom is increased, the sulfur utilizes more p-character in the bonding orbital directed towards atom X, amounting to an increase from $sp^{3.5}$ to $sp^{4.1}$ to $sp^{5.6}$ for compounds 4j-l (NH, O, and $NH_2^+$, respectively; hybridization values obtained from NBO analysis). This results in calculated S—X bond lengths of 1.67 Å, 1.62 Å and 1.88 Å for the same series, compared to the S—C length of 1.82 Å for compound 4j. In addition to changes in hybridization, anomeric effects also influence the S—X bond length. The endo-anomeric effect ($nX\rightarrow\sigma^*_{S-Y}$ and $nX\rightarrow\sigma^*_{S=O}$)) induces double bond character between the S and X, while the exo-anomeric effect ($nO\rightarrow\sigma^*_{S-X}$) lengthens the S—X bond. Thus, in the case of X=$NH_2^+$, the exo-anomeric effect is strengthened and there is no longer a lone pair to engage in the endo-anomeric effect.

More importantly, the reactivity of the alkyne is affected by both the acceptor ability of the propargylic heteroatom and the ring strain, where the angle at the proximal alkyne carbon increases from 157.2° to 158.8° to 159.5° for compounds 4k, 4j, and 4(O, NH, and $NH_2^+$, respectively). All of these derivatives display increased bending relative to the ~161° of compound 4i, but the lengthening of the S—N bond due to protonation outweighs the increased acceptor abilities in compound 4l. These findings are recapitulated by the distortion/interaction analysis (vide infra). In summary, the bond length, dictated by the identity of the heteroatom at the X position, has a substantial effect on the reactivity of the molecule, with the shortest bond lengths and relatively high electronegativity associated with propargylic oxygen atoms giving the highest reactivity. While electronic tuning via substitution at the propargylic nitrogen may provide for increased reactivity, the delicate balance of increased electronegativity competing with structural relaxation renders the free NH the most reactive of analogs which have been synthesized to date.

The effects of the homopropargylic heteroatom Y in 4 were investigated in a fashion similar to that described above for X. The substituents in the Y position were modified and X was fixed as a methylene group. The effects were surprisingly large, with over a 2 kcal/mol decrease in $\Delta E^\ddagger$ and $\Delta G^\ddagger$ noted. For the heteroatoms utilized experimentally (X=NH, Y=O), the effect of the homopropargylic oxygen in 4n is larger than that of the propargylic nitrogen in 4j. The increased reactivity as a result of homopropargylic heteroatoms stems from a slight increase in electrophilicity via inductive effects and also double hyperconjugation through exocyclic propargylic C—H bonds. These effects are moderated, however, by bond length alterations according to Bent's rule, as discussed above. This marks the first description of the participation of an endocyclic heteroatom at the homopropargylic positions in the reactivity of the strained alkyne.

Figure 3:
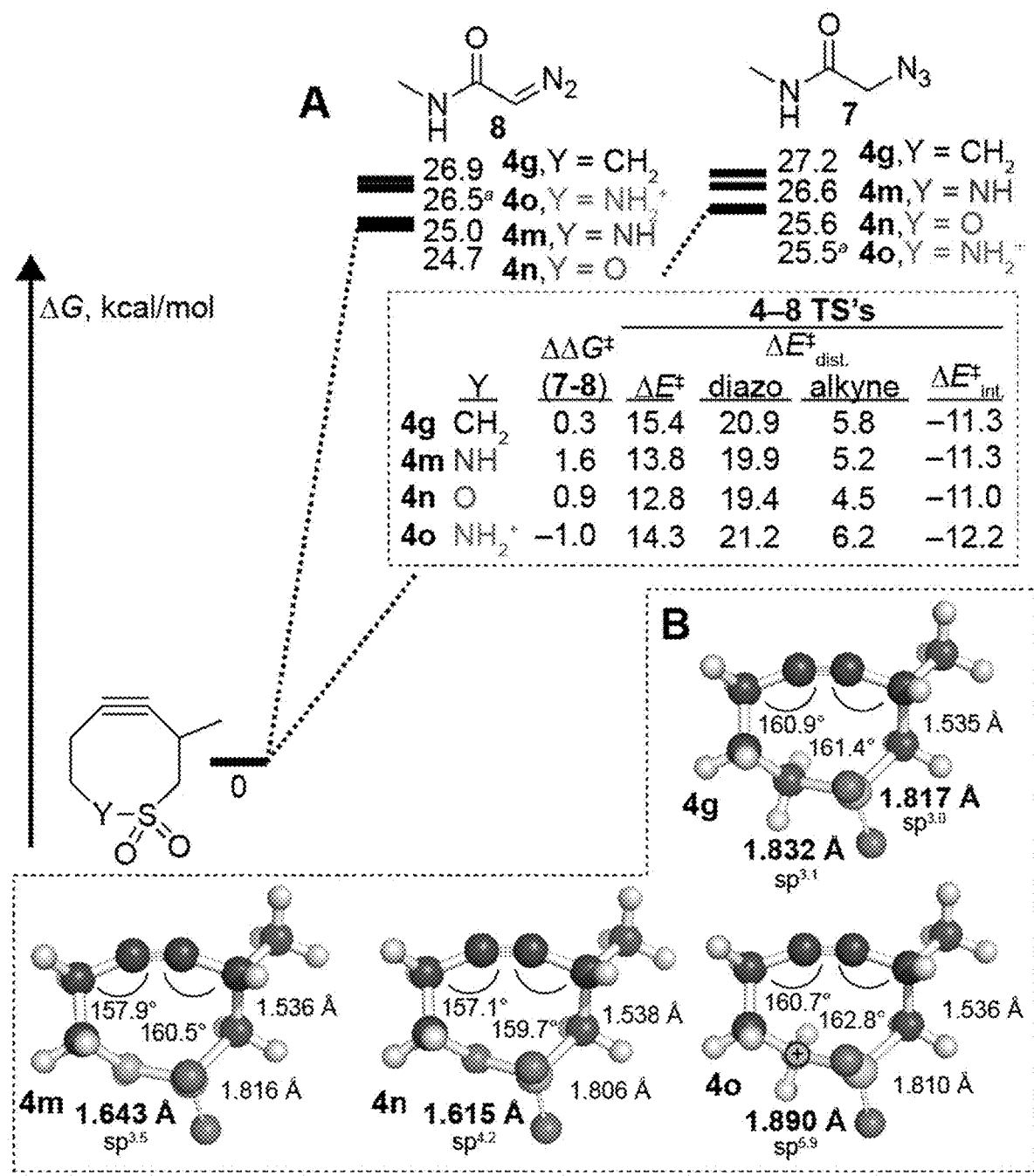
FIG. 3 is an illustration depicting, in panel A, the free energies of activation (kcal/mol) of the lowest energy transition states for each cycloadditions of diazo- and azidoacetamides reacting with alkynes containing various homopropargylic substituents. Geometries optimized at the M06-2X/6-311+G(d,p) level of theory with an IEFPCM solvent model for water (radii=UFF). Inset: Distortion/interaction analysis for cycloadditions of diazoacetamide. Panel B depicts the starting alkyne geometries with selected bond lengths given in Å and angles in degrees. Hybridizations obtained from NBO analysis given for sulfur bonding orbitals in S—Y bonds. Black=carbon; white=hydrogen; blue=nitrogen; red=oxygen; yellow=sulfur. $^a$Syn transition state is preferred.

Finally, the combination of the effects of both X and Y in 4 were explored. See FIG. 3. In many cases, synergistic effects of the propargylic and homopropargylic heteroatom were observed, resulting in increased reactivity when reacted with a standard alkyl azide 7 or diazoacetamide 8. As the ultimate goal was to simultaneously enhance both reactivity and selectivity, there was an interest in cases with improved reactivity where the $\Delta\Delta G\ddagger$ between the dipoles is also increased. Interestingly, this holds true in compounds 4w and 4v (X=$NH_2^+$ and Y=O or $NH_2^+$). In this situation, where there is no heteroatom at the Y position, favorable electronics were outweighed by unfavorable geometric relaxation. The sulfur atom must accommodate electronegative substituents at both the X and Y position, preventing the high p-character and bond lengthening in either of the two bonding orbitals (FIG. 3). This allows for both the large interactions provided by a highly electronegative propargylic heteroatom, without the counterproductive bond lengthening as a result of Bent's rule. This effect is readily apparent in compound 4s (X=Y=O), where the alkyne is bent to a significant degree as a result of significantly shortened S—X and S—Y bond lengths (<1.6 Ångstroms). Previous reports of decreased reactivity upon thioether incorporation are overcome when the endocylic sulfur atom must accommodate multiple electronegative atoms simultaneously. This provides a unique opportunity to alter alkyne distortion/strain electronically, rather than through the incorporation of annealed rings or additional $sp^2$ centers.

Figure 4:
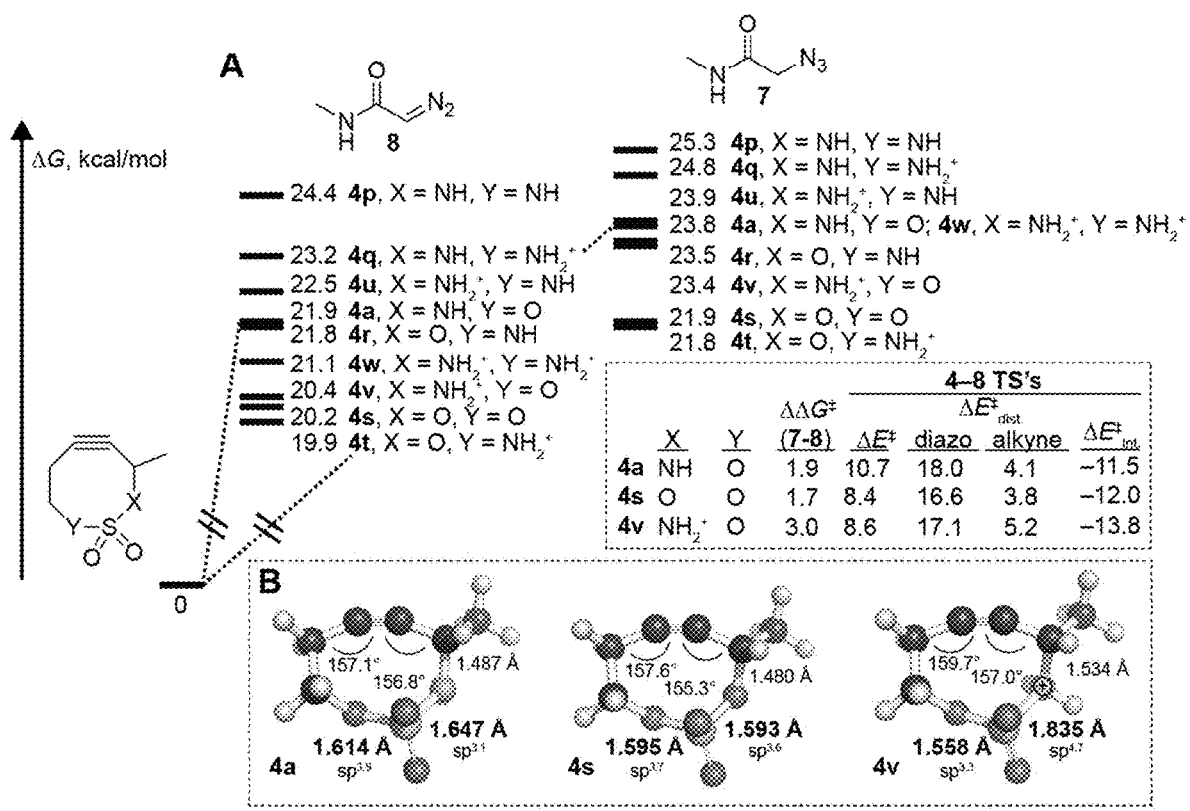
FIG. 4 is an illustration depicting, in panel A, the free energies of activation (kcal/mol) of the lowest energy transition states for each cycloadditions of diazo- and azidoacetamides reacting with alkynes containing various propargylic and homopropargylic substituents. Geometries optimized at the M06-2X/6-311+G(d,p) level of theory with an IEFPCM solvent model for water (radii=UFF). Inset: Distortion/interaction analysis for selected cycloadditions of diazoacetamide. Panel B depicts the starting alkyne geometries with selected bond lengths given in Ång-stroms and angles in degrees. Hybridizations obtained from NBO analysis given for sulfur bonding orbitals in S—X and S—Y bonds. Black=carbon; white=hydrogen; blue=nitrogen; red=oxygen; yellow=sulfur.
Figure 5:
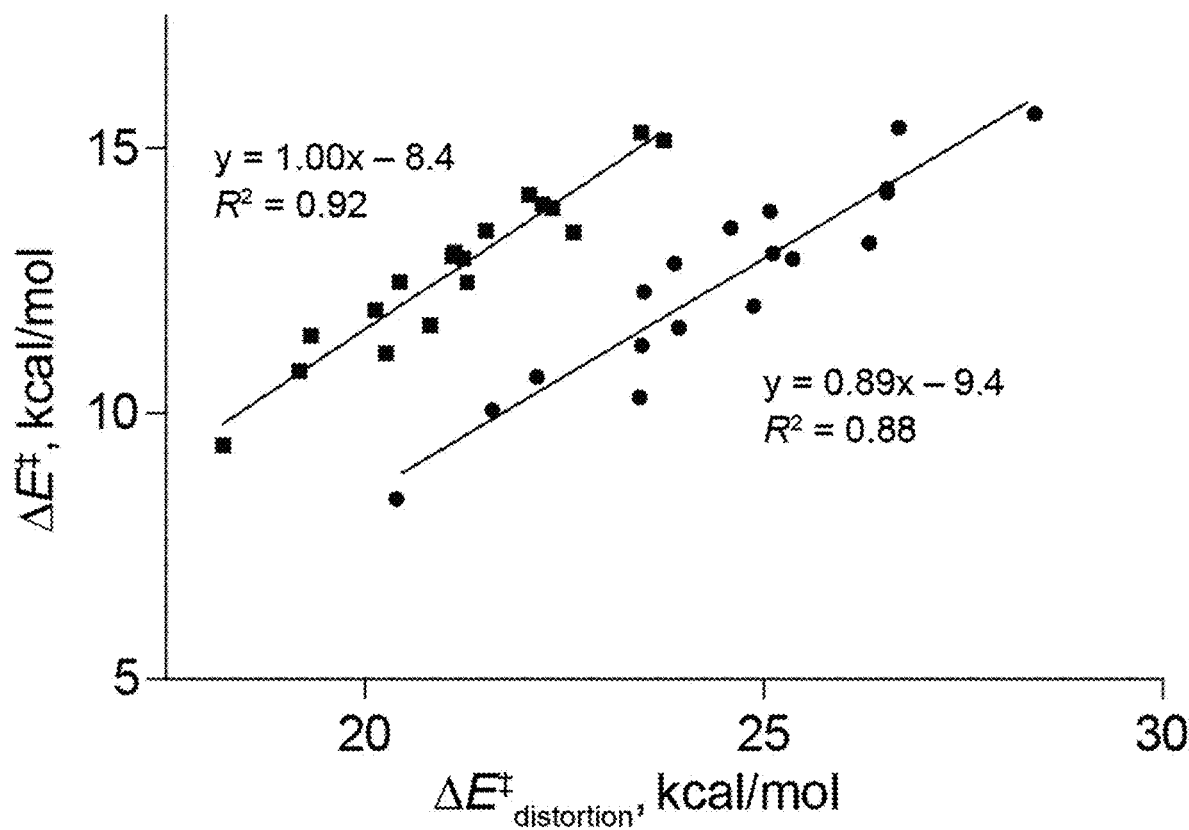
FIG. 5 is a series of superimposed plots of activation energies versus distortion energies split by the diazoacetamide (circles) and azidoacetamide (squares) for all cycloadditions evaluated to date, excluding charged alkynes.

Distortion/interaction (analogously termed strain activation) analysis was employed to elucidate structural effects on the reactivity of 4 when the identity of X and Y are varied (FIGS. 3, 4, and 5). In cases of a single heteroatom in either the X or Y position, the relatively short S—NH and S—O bonds, compared to S—C and S—$NH_2^+$, give decreased alkyne distortion energies (FIGS. 3 and 4). Due to increased S—$NH_2^+$ bond lengths, increased distortion energies are observed, however, large interactions partially compensate for the increased distortion energy.

When effects are combined and heteroatoms are placed at both the X and Y positions, the major effect is a decrease in the distortion energy rather than an increase in interactions. Charged species benefit from both a decrease in distortion energies and an increase in interaction energies—as a second heteroatom mediates the bond lengthening due to changes in hybridization—giving extremely low energies of activation.

While the distortion/interaction analysis accurately describes reactivity trends of each dipole with various alkynes (minus charged species that benefit from large interactions, FIG. 4), the analysis breaks down when plotting reactions of azide X and diazoacetamide Y together. This is due to the fact that stabilized diazoacetamides display artificially high distortion energies that are compensated for by increased interaction energies. Conjugative stabilization in the starting material is traded for bond formation, simultaneously increasing both distortion and interaction energies.

As a result of increased hyperconjugative interactions in the transition state, large interactions are observed for both X=O and $NH_2^+$. In the case of X=O, favorable interaction energies are accompanied by a decrease in distortion— previously described as assistance to alkyne bending accompanied by assistance to bond formation. In the case of X (and Y)=$NH_2^+$, however, the favorable interactions are negated by the increased distortion energies resulting from the geometric relaxation of the alkyne. As a result, inclusion of charged species into plots of activation energies against total distortion energies provides for very low correlation. When charged alkynes are removed, good correlation is observed, especially when each regioisomer is plotted independently.

In conclusion, disclosed herein are cyclooctynes bearing endocyclic heteroatoms that are able to tune alkyne electronics for varying degrees of reactivity amongst various 1,3-dipoles. Increased rates, high stability, and ease of synthesis relative to previously reported systems makes for an attractive compound for a number of applications.

The electronic nature of azido and diazo dipoles render this an ideal system for chemo- and regioselectivity in noncatalyzed 1,3-dipolar cycloadditions activated by strain. The current system allows for complete regioselectivity in reactions with diazoacetamides and the highest chemoselectivity reported between the diazo-acetamide and the analogous azide reacting with a cyclooctyne to date.

We have also unveiled a new method for the attenuation of strain in starting cycloalkynes. An interplay of anomeric effects and bond lengths dictated by hybridization is be predictably controlled by the choice of endocyclic heteroatoms.

Building Orthogonal Reactivity

Calculations predicted the ability to utilize the parent octyne and halogenated versions to achieve two orthogonal cycloadditions with tetrazines and diazoacetamides, respectively. This was also realized experimentally:

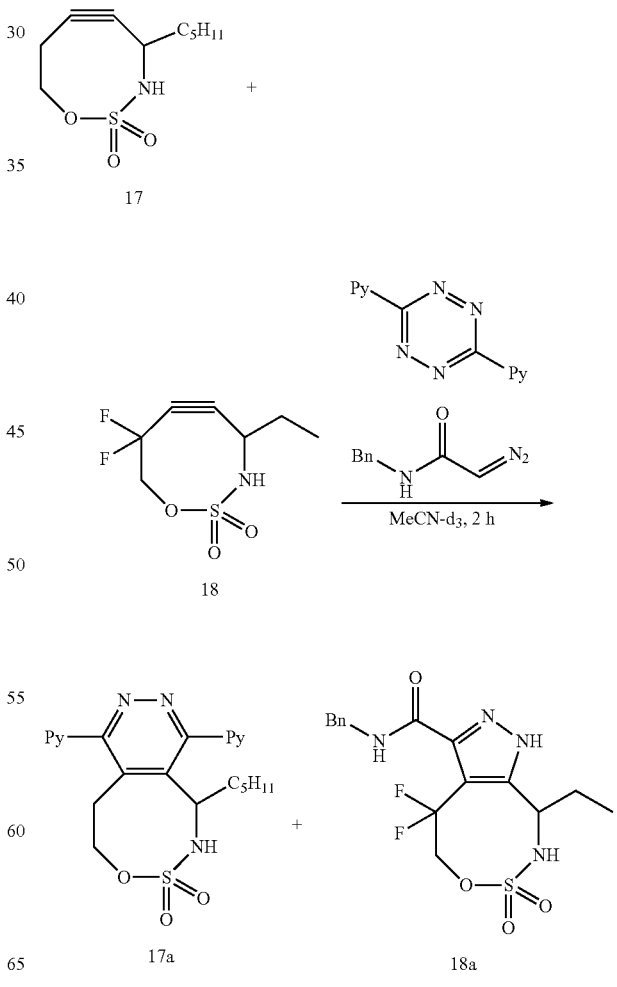

Table 4 shows the predicted reaction thermodynamics and rates:

TABLE 4

Gibbs free energies of activation (kcal/mol) and reaction rates for various cycloadditions using for mono-halogenated and di-halogenated octynes having sulfur, nitrogen, and oxygen heteroatoms (SNO-OCT):

| SNO-OCT | dipole | $\Delta G^{\ddagger}$ (kcal/mol) | Rate ($M^{-1}s^{-1}$) | $k_{rel}{}^d$ |
|---|---|---|---|---|
| 1 | diazoacetamide[a] | 19.3 | 4.75e−02 | 1.20e01 |
|   | azide[b] | 20.7 | 3.95e−03 | 1.00 |
|   | tetrazine[c] | 17.4 | 1.12 | 2.84e02 |
| 2a | diazoacetamide[a] | 16.6 | 4.51 | 8.88e03 |
|   | azide[b,e] | 19.9 | 1.65e−02 | 3.25e01 |
|   | tetrazine[c] | 21.9 | 5.08e−04 | 1.00 |
| 2b | diazoacetamide[a] | 15.9 | 1.38e01 | 1.02e05 |
|   | azide[b,e] | 19.2 | 5.28e−02 | 3.91e02 |
|   | tetrazine[c] | 22.7 | 1.35e−04 | 1.00 |
| 3b | diazoacetamide[a] | 14.7 | 1.07e02 | 2.65e05 |
|   | azide[b] | 18.0 | 3.96e−01 | 9.80e02 |
|   | tetrazine[c] | 22.1 | 4.04e−04 | 1.00 |

Geometries were optimized at B97D/6-311 + G(d,p) with CPCM solvent model (water)
[a]methyl diazoacetamide
[b]methyl azide
[c]dipyridyl tetrazine
[d]Relative rates across all dipoles for each SNO-OCT derivative
[e]syn TS is the lowest energy pathway The above derivatives can be made via Scheme 1, above, with adjustments to the reagents to yield various substituents on the two carbon atoms adjacent the triple bond. The synthesis of was both simple and flexible. See Scheme 2, below. Installing a silyl group at the allene carbon proximal to the sulfamate in 1 promoted regioselective aziridination at the distal alkene of the allene to furnish 2, due to the ability of the coplanar C—Si bond to stabilize the developing positive charge on the β carbon via hyperconjugation. Reaction of an intermediate silylated methyleneaziridine 2 with TBAF triggered a ring expansion to deliver the SNO-OCT 3. Important features of the SNO-OCT scaffold, as compared to conventional cycloalkynes, include the ability to tune the polarizability and reactivity of the triple bond, the ability to retain stability in the SNO-OCTs without significant loss in reactivity, and the lack of reaction towards glutathione and other nucleophiles present in the typical biological milieu.

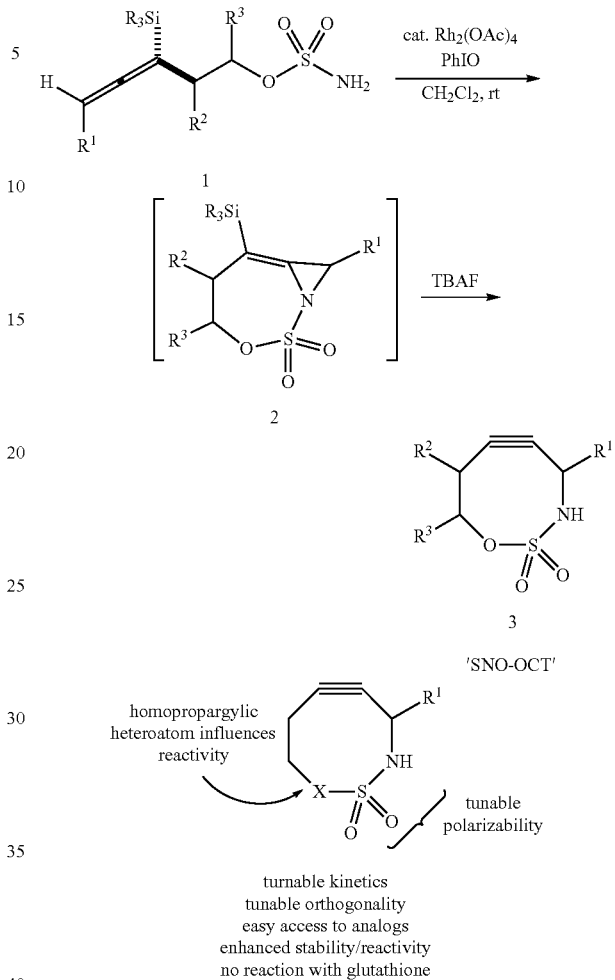

Scheme 2. Features of SNO-OCT strained cycloalkynes.

As illustrated in Scheme 3, addition of a lithium acetylide to propanaldehyde gave 9 in quantitative yield. Formation of the ester 10, followed by a Claisen rearrangement mediated by Zn/TMSCl and esterification furnished allene 11 in 76% yield over 2 steps. Ester reduction, formation of the sulfamate and tandem aziridination/TBAF-mediated ring expansion (as per Schemes 1 and 2) provided the di-halogenated (fluorinated) SNO-OCT 8a.

Scheme 3. Synthesis of fluorinated SNO-OCT

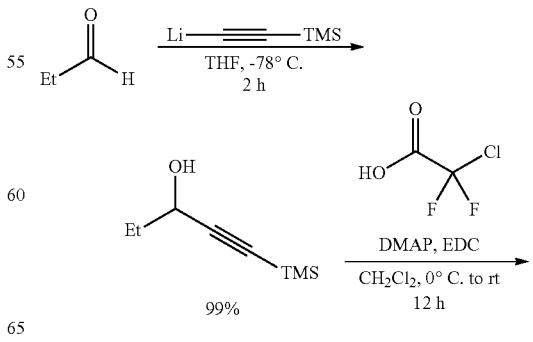

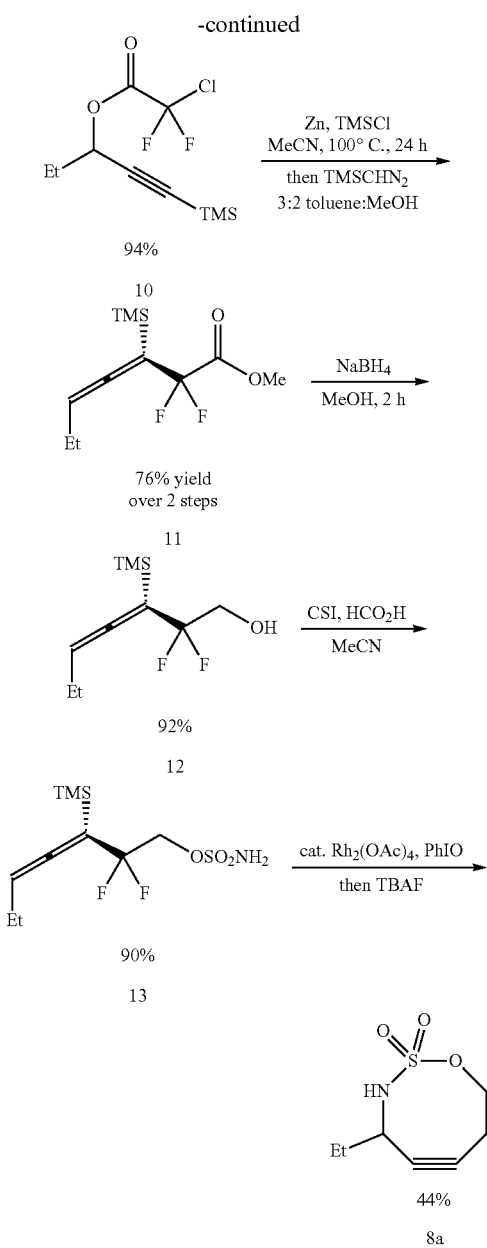

The ability to change the substitution pattern of the allene and the ease with which silylated bicyclic methyleneaziridine precursors to SNO-OCTs can be formed, stimulated our interest in understanding how the polarizability of the alkyne might be tuned to achieve two major goals: 1) to significantly increase the rates of reactions involving SNO-OCTs, and 2) to achieve mutually exclusive orthogonal reactivities of SNO-OCTs with Type I, Type II, and Type III dipoles in [3+2] and [4+2] cycloadditions. Other key advantages of SNO-OCTs include the ability to install multiple functional handles for appending dyes and other reporter molecules, water solubility, and precluding the reaction of the alkyne with thiols in the biological milieu.

Computational methods to predict the rates of reactions involving SNO-OCTs: The first major goal was to increase the rate of reaction of SNO-OCTs with various dipoles, without sacrificing either the stability of the ring or increasing the level of background reactions with other nucleophiles in the biological milieu, particularly thiols. It was felt that computational studies would be extremely helpful in predicting which modifications to the SNO-OCT would be most likely to result in significant rate enhancements.

The choice of computational methodology was key to achieving successful predictive capabilities; thus, we sought to identify the optimal screening tool to inform our experimental efforts. The M06-2X hybrid functional can be used for cycloaddition studies, but it has a tendency for activation barriers to be overestimated at this level of theory. See Y. Zhao & D. G. Truhlar (2006) "The M06 suite of density functionals for main group thermochemistry, thermochemical kinetics, noncovalent interactions, excited states, and transition elements: Two new functionals and systematic testing of four M06-class functionals and 12 other functionals," Theor Chem Acc. 120 (1-3): 215-241. To account for this deviation, a correction factor based on experimental $2^{nd}$-order rate constants, is applied to the computed values to bring them into better quantitative agreement. Similarly, it has been found that M06-2X overestimates activation barriers in strain-promoted oxidation-controlled quinone (SPOCQ) cycloadditions. In the case of SNO-OCTs, density functional theory (DFT) calculations initially conducted at the M06-2X level of theory with a 6-311++G(d,p) basis set using Gaussian 16 (Gaussian, Inc., Wallingford, Conn.) also showed that the predicted rates, and even relative trends in rate, deviated significantly from the experimental values. This suggested that a different level of theory might be more suitable for the SNO-OCT systems. Thus, transition state models were optimized using a B97D functional with the Conductor-like Polarizable Continuum Model (CPCM) for the solvent (Table 5). This change in the level of theory led to a marked improvement in computed reaction rates, predicting a 0.0040 $M^{-1}s^{-1}$ reaction rate ($CD_3CN$) for the reaction of the parent SNO-OCT 4 with $MeN_3$, a result within an order of magnitude of experimental (0.026 $M^{-1}s^{-1}$) data for the reaction of 4 with $BnN_3$ (Table 5, entry 1). The presence of the hydroxyl group in 5 increased the $2^{nd}$-order rate constant in the reaction with azides both experimentally and computationally (entry 2), showing that although the absolute rates are still not accurate, the trend may be predicted. However, one limitation of this computational method is that the rate increase observed experimentally when moving from $CD_3CN$ to a 2:1 $D_2O:CD_3CN$ mixture is not well-reflected in the computational results. The lack of ability for DFT methods to accurately model solvents is well-known. While this caveat should be kept in mind, the B97D functional does enable valuable predictions of how changes to the SNO-OCT structure might be expected influence the rates of 1,3-dipolar cycloadditions with azides and diazoalkanes.

TABLE 5

B97D/6-311 + G(d,p) calculated reaction rates are in agreement with experimentally determined kinetics for various SNO-OCT/dipole cycloadditions.

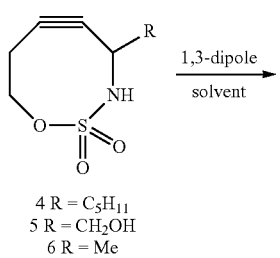

4 R = $C_5H_{11}$
5 R = $CH_2OH$
6 R = Me

TABLE 5-continued

[Structures shown: anti and syn isomers of SNO-OCT products with R¹, Y, Z, X substituents and NH, S(=O)₂, O functional groups]

| | Experimental[a] | | | Calculated[b] | | |
|---|---|---|---|---|---|---|
| entry | SNO-OCT | dipole | Rate ($M^{-1}s^{-1}$) | SNO-OCT | dipole | Rate ($M^{-1}s^{-1}$) |
| 1 | 4 | Bn—$N_3$ | $2.60 \times 10^{-2}$ | 6 | Me—$N_3$ | $3.95 \times 10^{-3}$ |
| 2 | 5 | Bn—$N_3$ | $8.70 \times 10^{-2}$ ($1.30 \times 10^{-1}$) | 5 | Me—$N_3$ | $1.43 \times 10^{-2}$ ($1.40 \times 10^{-2}$) |
| 3 | 4 | Bn-NH-C(O)-CH=$N_2$ | $2.70 \times 10^{-1}$ | 6 | Me-NH-C(O)-CH=$N_2$ | $4.75 \times 10^{-2}$ |

[a]Experimental rates determined in $CD_3CN$ or 2:1 $D_2O$:$CD_3CN$
[b]Geometries optimized at B97D/6-311 + G(d,p); CPCM solvent model ($H_2O$ or $CD_3CN$)

Another compelling feature of SNO-OCTs is their preference for reaction with diazoalkanes over azides, highlighting their potential for use in orthogonal reactions. As an ideal computational method should also be capable of predicting orthogonality, we constructed TS models for the reactions of 4 and 6 with azide and diazoacetamide dipoles (Table 5, entries 1 and 3). Despite the fact that computed models were truncated versions of the experimental substrates, the predicted chemo selectivity (12:1) favored the reaction of the methyl diazoacetamide over methyl azide in a ratio of 12:1; this was in excellent agreement with experimental results (10:1).

New SNO-OCT derivatives for increasing reaction rate: Halogenated SNO-OCT compounds with the halogen substituent(s) at various positions in the SNO-OCT scaffold were then explored. These modifications were first explored computationally by comparing the Gibbs free energies of activation and predicted reaction rates for a parent SNO-OCT 6 and two proposed difluorinated derivatives 7 and 8 (Table 6) with the 1,3-dipoles methyl diazoacetamide and methyl azide. With all three SNO-OCTs 6-8, computations predict that installation of homopropargylic fluorines in 7 will decrease the reaction rate with both 1,3-dipoles relative to the parent SNO-OCT 6. In contrast, placing the two fluorines at the propargylic carbon in 8 is predicted to increase the rate of its reaction with $MeN_3$ by an order of magnitude as compared to 6. Interestingly, computations also predicted that 8 should be almost 300 times more reactive towards methyl diazoacetamide, as compared to 6. This exciting result shows that the reactivity of the core scaffold can be adjusted to improve reaction rates and to yield purposefully designed pairs of mutually bioorthogonal SNO-OCTs.

TABLE 6

Gibbs free energies of activation (kcal/mol) and reaction rates for fluorinated SNO-OCTs with Me diazoacetamide and $MeN_3$.

[Structures shown: SNO-OCT scaffold with X', R substituents; reaction with 1,3-dipole gives anti and syn products]

6 R = Me; X' = H
7 R = $CF_2CH_3$, X' = H
8 R = Me, X' = F

[Dipole shown: Me-NH-C(O)-CH=$N_2$]

| | 1,3-dipole $MeN_3$ | | | Me-NH-C(O)-CH=$N_2$ | | |
|---|---|---|---|---|---|---|
| SNO-OCT | $\Delta G^{\ddagger}$ (kcal/mol) | $k_2$ ($M^{-1}s^{-1}$) | $k_{rel}$[c] | $\Delta G^{\ddagger}$ (kcal/mol) | $k_2$ ($M^{-1}s^{-1}$) | $k_{rel}$[c] |
| 6 | 20.7 | $3.95 \times 10^{-3}$ | 1.00 | 19.3 | $4.75 \times 10^{-2}$ | 1.00 |
| 7 | 22.3 | $2.57 \times 10^{-4}$ | $6.51 \times 10^{-2}$ | 20.3[b] | $8.27 \times 10^{-3}$ | $1.70 \times 10^{-1}$ |
| 8 | 19.2[b] | $5.28 \times 10^{-2}$ | $1.34 \times 10^{1}$ | 15.9 | $1.38 \times 10^{1}$ | $2.91 \times 10^{2}$ |

[a]Geometries optimized at B97D/6-311 + G(d,p); CPCM solvent model ($H_2O$).
[b]syn TS is lowest energy pathway.
[c]Relative rates across all SNO-OCTs for specified dipole.

With the difluorinated SNO-OCT 8a in hand, preliminary kinetic studies were carried out (Table 7) and compared to computed and experimental rates of both the parent SNO-OCTs 4 and 6, as well as 8. A rate enhancement of 13-fold was predicted in moving from the parent SNO-OCT 6 (entry 1, right column) to the difluorinated SNO-OCT 8 (entry 3, right column) in reactions with alkyl azides; this was quite similar to the experimental rate enhancement seen in moving from 4 to 8a of 18× (entries 1 and 3 in the left column).

A rate enhancement of ~300-fold was predicted in moving from the parent SNO-OCT 6 (entry 2, right column) to the difluorinated SNO-OCT 8 (entry 4, right column) in reactions with alkyl diazaoacetamides. Experimentally, the rate enhancement in moving from 4 to 8a (entries 2 and 4 in the left column) could not be determined using proton NMR spectroscopy to monitor the progress of the reaction. However, this result suggests that the second order rate constant is likely to be significantly higher ≥1 $M^{-1}s^{-1}$. These results further stimulated our interest in exploiting the preference for reaction of fluorinated SNO-OCTs with diazoalkanes over their non-fluorinated SNO-OCT counterparts. While orthogonality was also observed for reactions of 4 and 8a with azides, the selectivity appeared to be lower than that predicted for the diazoalkanes.

TABLE 7

Comparison of experimental and calculated (B97D/6-311 + G(d,p)) rate constants in cycloadditions of SNO-OCTs with azide and diazoacetamide 1,3-dipoles.

| | | Experimental[a] | | | Calculated[b] | |
|---|---|---|---|---|---|---|
| entry | SNO-OCT | dipole | Rate ($M^{-1}s^{-1}$) | SNO-OCT | dipole | Rate ($M^{-1}s^{-1}$) |
| 1 | 4 | Bn—$N_3$ | $2.60 \times 10^{-2}$ | 6 | Me—$N_3$ | $3.95 \times 10^{-3}$ |
| 2 | see Table 1<br>4 | | $2.70 \times 10^{-1}$ | 6 | | $4.75 \times 10^{-2}$ |
| 3 | 8a | Bn—$N_3$ | $4.60 \times 10^{-1}$ | 8 | Me—$N_3$ | $5.30 \times 10^{-2}$ |
| 4 | 8a | | >1M | 8 | | $1.38 \times 10^{1}$ |

[a]Experimental rates determined in $CD_3CN$
[b]Geometries were optimized at B97D/6-311 + G(d,p); CPCM solvent model (water)

The outcome of these SPAAC-type reactions can also be controlled by substituting one or both of the propargylic carbon atoms in the octyne ring with substituents having different potential hydrogen bond donor and acceptor sites. This, for example the electrophilicity of the alkyne moiety can be steadily increased, for example, according to the following series of compounds:

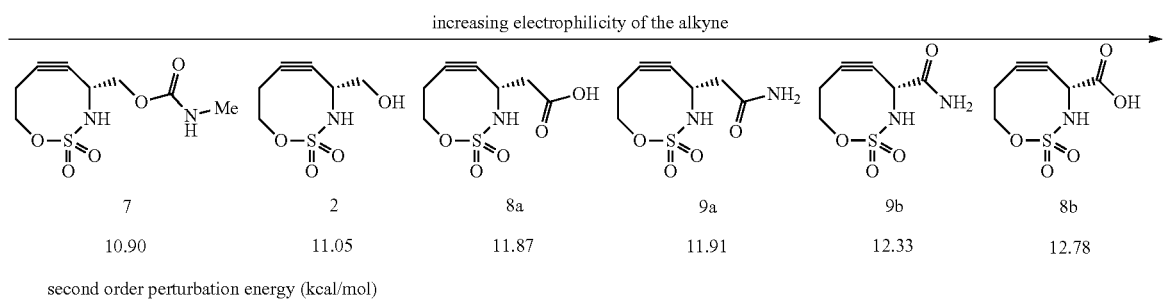

increasing electrophilicity of the alkyne

| 7 | 2 | 8a | 9a | 9b | 8b |
|---|---|---|---|---|---|
| 10.90 | 11.05 | 11.87 | 11.91 | 12.33 | 12.78 | second order perturbation energy (kcal/mol)

The same substituent may also be used at the other propargylic carbon item, for example,

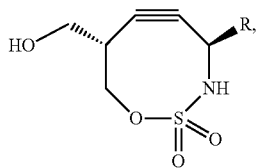

etc.

In short, the ability to "tune" the alkyne electrophilicity via rationally selected substituents at the propargylic carbon atoms allowed for mutually orthogonal Type 1/Type III cycloadditions. See, for example, Scheme 4:

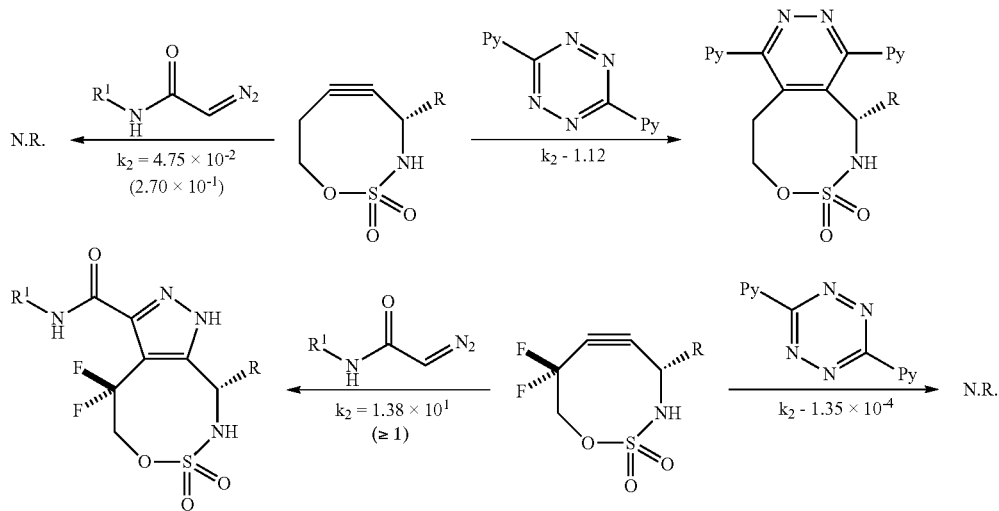

In the top reaction, the left-hand propargylic carbon atom of the octyne ring is unsubstituted. The leftward reaction, with the diazoacetamide, does not occur. The rightward reaction, with the tetrazine, proceeds readily. The exact reverse is true when the left-hand propargylic carbon atom is di-halo substituted, as shown in the bottom reaction of Scheme 4. In the bottom reaction, the left-hand propargylic carbon atom is di-halo substituted. Here, the rightward reaction (with the tetrazine) does not occur. The leftward reaction, though, with the diazoacetamide, proceeds readily.

What is claimed is:

1. A compound of Formula I:

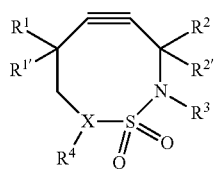

wherein:

$R^1$ and $R^{1'}$ are independently selected from hydrogen, halogen, $C_1$-to-$C_{12}$ linear or branched hydroxyalkyl, $C_1$-to-$C_{12}$ linear or branched halo-alkyl, carboxy, carboxyalkyl, amido, N-alkylamido, N,N-dialkylamido, carbamoyloxy, N-alkylcarbamoyloxy, and N,N-dialkylcarbamoyloxy, provided that that $R^1$ and $R^{1'}$ are not simultaneously hydrogen;

$R^2$ and $R^{2'}$ hydrogen, halogen, $C_1$-to-$C_{12}$ linear or branched alkyl, $C_1$-to-$C_{12}$ linear or branched hydroxyalkyl, $C_1$-to-$C_{12}$ linear or branched halo-alkyl, carboxy, carboxyalkyl, amido, N-alkylamido, N,N-dialkylamido, carbamoyloxy, N-alkylcarbamoyloxy, and N,N-dialkylcarbamoyloxy, provided that that $R^2$ and $R^{2'}$ are not simultaneously hydrogen;

$R^3$ is selected from hydrogen, $C_1$ to $C_{12}$ linear or branched alkyl, and nitrogen protecting groups;

X is oxygen or nitrogen;

when X is oxygen, $R^4$ is absent; and when X is nitrogen, $R^4$ is selected from H, $C_1$-to-$C_{12}$ linear or branched alkyl, and nitrogen protecting groups.

2. The compound of claim 1, wherein X is oxygen.

3. The compound of claim 1, wherein X is nitrogen.

4. The compound of claim 1, wherein X is oxygen and at least one of $R^1$ or $R^{1'}$ is halogen.

5. The compound of claim 4, wherein $R^1$ and $R^{1'}$ are halogen.

6. The compound of claim 4, wherein at least one of $R^1$ and $R^{1'}$ are fluorine.

7. The compound of claim 4, wherein $R^1$ and $R^{1'}$ are fluorine.

8. The compound of claim 4, wherein at least one of $R^2$ and $R^{2'}$ is $C_1$-to-$C_{12}$ linear or branched alkyl or $C_1$-to-$C_{12}$ linear or branched hydroxyalkyl.

9. The compound of claim 4, wherein at least one of $R^2$ and $R^{2'}$ is $C_1$-to-$C_{12}$ linear or branched halo-alkyl.

10. The compound of claim 4, wherein at least one of $R^2$ and $R^{2'}$ is carboxy or carboxyalkyl.

11. The compound of claim 4, wherein at least one of $R^2$ and $R^{2'}$ is amido, N-alkylamido, N,N-dialkylamido, carbamoyloxy, N-alkylcarbamoyloxy, or N,N-dialkylcarbamoyloxy.

12. The compound of claim 1, wherein X is nitrogen and at least one of $R^1$ or $R^{1'}$ is halogen.

13. The compound of claim 12, wherein $R^1$ and $R^{1'}$ are halogen.

14. The compound of claim 12, wherein at least one of $R^1$ and $R^{1'}$ are fluorine.

15. The compound of claim 12, wherein $R^1$ and $R^{1'}$ are fluorine.

16. The compound of claim 12, wherein at least one of $R^2$ and $R^{2'}$ is $C_1$-to-$C_{12}$ linear or branched alkyl or $C_1$-to-$C_{12}$ linear or branched hydroxyalkyl.

17. The compound of claim 12, wherein at least one of $R^2$ and $R^{2'}$ is $C_1$-to-$C_{12}$ linear or branched halo-alkyl.

18. The compound of claim 12, wherein at least one of $R^2$ and $R^{2'}$ is carboxy or carboxyalkyl.

19. The compound of claim 12, wherein at least one of $R^2$ and $R^{2'}$ is amido, N-alkylamido, N,N-dialkylamido, carbamoyloxy, N-alkylcarbamoyloxy, or N,N-dialkylcarbamoyloxy.

20. The compound of claim 12, wherein $R^4$ is H.

21. The compound of claim 12, wherein $R^4$ is $C_1$-to-$C_{12}$ linear or branched alkyl.

22. Compounds of claim 12, wherein $R^4$ is a nitrogen protecting group.

23. A method of forming chemical bonds, the method comprising reacting a first compound of Formula I:

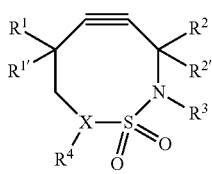

(Formula I)

wherein:

$R^1$ and $R^{1'}$ are independently selected from hydrogen, halogen, $C_1$-to-$C_{12}$ linear or branched hydroxyalkyl, $C_1$-to-$C_{12}$ linear or branched halo-alkyl, carboxy, carboxyalkyl, amido, N-alkylamido, N,N-dialkylamido, carbamoyloxy, N-alkylcarbamoyloxy, and N,N-dialkylcarbamoyloxy, provided that that $R^1$ and $R^{1'}$ are not simultaneously hydrogen;

$R^2$ and $R^{2'}$ hydrogen, halogen, $C_1$-to-$C_{12}$ linear or branched alkyl, $C_1$-to-$C_{12}$ linear or branched hydroxyalkyl, $C_1$-to-$C_{12}$ linear or branched halo-alkyl, carboxy, carboxyalkyl, amido, N-alkylamido, N,N-dialkylamido, carbamoyloxy, N-alkylcarbamoyloxy, and N,N-dialkylcarbamoyloxy, provided that that $R^2$ and $R^{2'}$ are not simultaneously hydrogen;

$R^3$ is selected from hydrogen, $C_1$ to $C_{12}$ linear or branched alkyl, and nitrogen protecting groups;

X is oxygen or nitrogen;

when X is oxygen, $R^4$ is absent; and when X is nitrogen, $R^4$ is selected from H, $C_1$-to-$C_{12}$ linear or branched alkyl, and nitrogen protecting groups;

with a second compound comprising a 1,3-dipole, in a 1,3-cycloaddition reaction.

* * * * *